US006248352B1

(12) United States Patent
Semeria et al.

(10) Patent No.: US 6,248,352 B1
(45) Date of Patent: Jun. 19, 2001

(54) COMPOSITIONS CONTAINING LIPID COMPOUNDS DERIVED FROM SPHINGOID BASES, THEIR PROCESS OF PREPARATION

(75) Inventors: Didier Semeria, Courtry; Michel Philippe, Wissous, both of (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 09/265,392

(22) Filed: Mar. 10, 1999

(30) Foreign Application Priority Data

Mar. 10, 1998 (FR) .................................................. 98 02915

(51) Int. Cl.$^7$ ........................... A61K 9/127; A61K 31/56
(52) U.S. Cl. ........................ 424/450; 424/400; 424/401; 424/45; 424/59; 424/61; 424/62; 424/63; 424/65; 424/70.1; 424/70.27; 424/70.6; 424/76.1; 424/195.1; 514/178; 514/937; 514/938; 514/943; 514/944; 514/945; 514/844; 514/880; 514/881; 514/886; 514/887
(58) Field of Search .................................... 424/400, 450, 424/401; 564/506, 503, 355; 514/846, 847, 937, 938, 178

(56) References Cited

U.S. PATENT DOCUMENTS

| | | | |
|---|---|---|---|
| 5,149,860 | 9/1992 | Zysman et al. | 560/160 |
| 5,198,470 | 3/1993 | Zysman et al. | 514/785 |
| 5,665,778 | * 9/1997 | Semeria et al. | 514/613 |

FOREIGN PATENT DOCUMENTS

| | | |
|---|---|---|
| 0 420 722 | 4/1991 | (EP) . |
| 1 477 048 | 4/1967 | (FR) . |
| 2 091 516 | 1/1972 | (FR) . |
| 2 315 991 | 1/1977 | (FR) . |
| 2 465 780 | 3/1981 | (FR) . |
| 2 482 128 | 11/1981 | (FR) . |
| 2 652 002 | 3/1991 | (FR) . |
| WO 83/01571 | 5/1983 | (WO) . |
| WO 92/08685 | 5/1992 | (WO) . |

OTHER PUBLICATIONS

English language Derwent Abstract of FR 2 091 516.
English language Derwent Abstract of FR 2 315 991.
English language Derwent Abstract of FR 2 465 780.
English language Derwent Abstract of FR 2 482 128.
English language Derwent Abstract of FR 2 652 002.
Bruno Bernet et al., "Enantioselective Synthesis of D–erythro–Sphingosine", Tetrahedron Letters, vol. 24, No. 49, 1983, pp. 5491–5494.
Makoto Kiso et al., "A Novel Route to D–erythro–Sphingosine and Related Compounds From Mono–O–Isopropylidene–D–Xylose or –D–Galactose", Carbohydrate Research, vol. 158, 1986, pp. 101–111.
Richard R. Schmidt, "Synthesis of D–erythro–Sphingosines", Tetrahedron Letters, vol. 27, No. 4, 1986, pp. 481–484.
Prof. Dr. H. A. Staab, "Synthesis Using Heterocyclic Amides (Azolides)", Angew. Chem. internat. Edit., vol. 1, No.7, 1962, pp. 351–367.
Francis Zoka, Jr. et al., "Procedure for Preparation of Liposomes With Large Internal Aqueous Space and High capture by Reverse–Phase Evaporation", Proc. Natl. Acad. Sci., vol. 75, No. 9, 1978, pp. 4194–4198.

* cited by examiner

Primary Examiner—Thurman K. Page
Assistant Examiner—Lakshmi Channavajjala
(74) Attorney, Agent, or Firm—Finnegan, Henderson, Farabow, Garrett & Dunner, L.L.P.

(57) ABSTRACT

The invention encompasses compounds corresponding to the formula

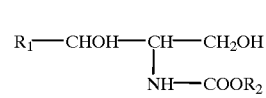

(I)

in which
  $R_1$ denotes a $C_1$–$C_{31}$, preferably $C_9$–$C_{25}$, hydrocarbon-comprising radical, in particular a saturated or unsaturated, linear or branched, $C_1$–$C_{31}$, preferably $C_9$–$C_{25}$, alkyl radical which can be substituted by one or more optionally esterified hydroxyls; and $OR_2$ denotes a cholesteryl radical; the said compounds being in the form of a pure enantiomer or in the form of a mixture of isomers. The invention also relates to their process of preparation and to their use, in particular for the treatment and care of the skin, hair, nails and eyelashes, in cosmetics or in dermatology.

36 Claims, No Drawings

COMPOSITIONS CONTAINING LIPID COMPOUNDS DERIVED FROM SPHINGOID BASES, THEIR PROCESS OF PREPARATION

The invention encompasses novel lipid compounds derived from sphingoid bases, the process of preparation and their use, in particular for the treatment and care of the skin, hair, nails and eyelashes, in cosmetics or in dermatology.

Exposure of the skin to cold, to the sun or to atmospheres with a low relative humidity, repeated treatments with washing compositions or contact with organic solvents, are factors which result in a visible drying to various degrees. The skin appears drier and less supple and the skin contours appear more pronounced. Furthermore, hair which is subjected too often to certain hair treatments loses its glossy appearance and can become coarse and brittle.

The inventors have thus sought for compounds which make it possible to prevent or to correct these phenomena, which are reflected by visible drying, and which restore the skin's suppleness and the hair's gloss and softness.

In order to solve this problem, provision has already been made, in particular in French Patent 2,652,002, for the use of lipid compounds. These compounds, when used in cosmetic or dermatological compositions for the treatment and care of the skin and hair, have a moisturizing effect which makes it possible to prevent or to correct certain effects of visible drying of the skin or hair. However, it would be desirable to develop compounds which, when used in cosmetic or dermatological compositions, have a moisturizing or treating effect superior to that of the compounds of this patent.

One aspect of the invention is therefore novel lipid compounds derived from sphingoid bases corresponding to the formula:

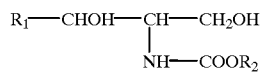
(I)

in which
$R_1$ denotes a $C_1$–$C_{31}$, preferably $C_9$–$C_{25}$, hydrocarbon-comprising radical, in particular a saturated or unsaturated, linear or branched, $C_1$–$C_{31}$, preferably $C_9$–$C_{25}$, hydrocarbon radical which can be substituted by one or more optionally esterified hydroxyls; $OR_2$ denotes a cholesteryl radical; the said compounds being in the form of a pure enantiomer or in the form of a mixture of isomers.

Preferred compounds of formula (I), are, for example:
N-(cholesteryloxycarbonyl)-2-aminooctadecane-1,3-diol;
N-(cholesteryloxycarbonyl)-2-aminooctadecane-1,3,4-triol;
the said compounds being in the pure form or in the form of mixtures of isomers.

The lipid compounds of formula (I) above are somewhat similar in their structure to ceramides, which are the main constituents of the intercorneocytic lipids of the stratum corneum. It is generally accepted that they participate in maintaining the integrity of the cutaneous barrier. They are also found, to a lesser extent, in the hair.

The compounds of formula (I) according to the invention can therefore be of very particular advantage in the treatment and care of the skin, hair, nails and eyelashes in cosmetics or in dermatology, the moisturizing effects of which are substantially greater than those of lipid compounds derived from sphingoid bases of the prior art, in particular those in French Patent 2,652,002.

The lipid compounds of formula (I) are satisfactorily harmless with respect to the skin, hair, nails, eyelashes, eyebrows and mucous membranes. They have good emollient and softening properties. They are easily dissolved in the fatty phases of cosmetic and dermopharmaceutical preparations.

Furthermore, hair treated with these compounds of formula (I) can exhibit a glossy appearance, a softer feel and a reduced sensitivity to water, due to the contribution of lipid matter uniformly distributed over the scales of the hair. The mechanical and liveliness properties can also be improved.

The compounds according to the invention can form vesicles with other lipids.

The lipid compounds according to the invention of formula (I) above can be obtained by the condensation on the amine functional group of a sphingoid base of the following formula (II):

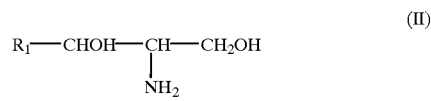
(II)

in which $R_1$ has the same meaning indicated in formula (I), with either a cholesteryl chloroformate of the following formula (III):

(III)

in which $OR_2$ has the same meaning indicated in the formula (I), in an appropriate organic solvent in the presence of a base; or with the cholesteryl imidazolide of following formula (IV):

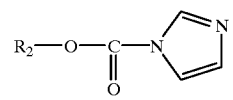
(IV)

in which $OR_2$ has the same meaning indicated in the formula (I).

The process for the preparation of the compounds of formula (I) can be represented by the following scheme:

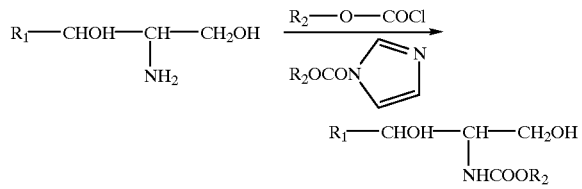

$R_1$ and $OR_2$ having the meanings indicated above.

The compounds of formula (I) can be obtained either by reaction of the compounds of formula (II) with the chloroformate (III) in solvents, such as tert-butyl methyl ether, dimethylformamide or tetrahydrofuran (THF), in the presence of a base, such as, for example, triethylamine, pyridine, sodium bicarbonate, and the like, or by reaction of the compounds of formula (II) with the imidazolide (IV), which is isolated or prepared in situ, for example by reaction of a fatty alcohol with carbonyldiimidazole.

Cholesteryl chloroformate is a commercial product. Cholesteryl imidazolide is synthesized according to the methods described by H. A. Staab in Angew. Chem. International Edit., Vol. 1 (1962), No. 7, p. 351, the disclosure of which is specifically incorporated by reference herein.

The hydrochloride of the compound of formula (II) may also be used in the preparation of the compound of formula (I).

The compounds of formula (II) are known compounds. Their synthesis has been described in particular by D. Shapiro in "Chemistry of Sphingolipids", Hermann, Paris (1969), the disclosure of which is specifically incorporated by reference herein.

The synthetic processes described above result in racemic mixtures. It is possible to obtain compounds in the form of pure enantiomers by carrying out a resolution of the racemate described by Shapiro in the above mentioned article on page 99. Pure enantiomers can also be synthesized directly according to the processes described by R. Schmidt in "Tetrahedron Letters", Vol. 27, No. 4, pages 481–484 (1986), the disclosure of which is specifically incorporated by reference herein, by B. Bernet in the same journal, Vol. 24, No. 49, pages 5491–5494 (1983), the disclosure of which is specifically incorporated by reference herein, or by Makoto Kiso in "Carbohydrate Research", 158 (1986), pages 101–111, the disclosure of which is specifically incorporated by reference herein.

The lipid compounds according to the invention of formula (I) can have various applications, in particular in cosmetic and dermatological compositions. In addition, these compounds possess the property of forming vesicles in combination with other lipids, when they are dispersed in water.

One aspect of the invention is therefore the use of the compounds of formula (I) in emulsions or dispersions or in lotions. Another aspect of the invention is the use of these compounds, in combination with other lipids, for the formation of lipid spherules.

Another aspect of the invention is compositions for cosmetic or dermatological use comprising, in a cosmetically acceptable medium, at least one of the compounds of formula (I) as defined above.

Yet another aspect of the invention is a process for the cosmetic treatment of the skin, hair, nails, eyelashes or eyebrows which comprises applying to the skin, hair, nails, eyelashes or eyebrows a sufficient amount of such a composition comprising the compounds of formula (I).

Generally, the compositions according to the invention can be in the form of emulsions (milk or cream); aqueous/alcoholic, oily or oleoalcoholic lotions; gels; dispersions or solid sticks; or an aerosol foam or sprays.

According to the invention, the compounds of formula (I) are preferably present in an amount ranging from 0.005% to 20%, more preferably from 0.01 to 10%, of the total weight of the composition.

The compositions are, for example, emollient lotions, milks or creams; milks or creams for caring for the skin or hair; make-up removal creams, lotions or milks; foundation bases; anti-sun lotions, milks or creams; artificial tanning lotions, milks or creams; shaving creams or foams; aftershave lotions; shampoos; lip rouges; mascaras or nail varnishes.

These compositions may also be in the form of lipsticks, intended either to colour the lips or to avoid chapping, make-up products for the eyes or rouges and foundations for the face.

When the compositions according to the invention are provided in the form of emulsions of water-in-oil or oil-in-water type, the fatty phase preferably comprises a mixture of compounds of formula (I) with at least one oil, and optionally one other fatty substance.

Preferably, the fatty phase of the emulsions can constitute from 5 to 60% of the total weight of the emulsion. The aqueous phase of the emulsions preferably constitutes from 30 to 85% of the total weight of the emulsion. The proportion of emulsifying agent preferably ranges from 1 to 20% and more preferably from 2 to 12% of the total weight of the emulsion.

When the compositions according to the invention are in the form of oily, oleoalcoholic or aqueous/alcoholic lotions, they may constitute, for example, anti-sun lotions comprising a screening agent which absorbs UV rays or skin-softening lotions; the oily lotions can additionally constitute foaming oils comprising an oil-soluble surfactant, bath oils, and the like.

Preferred adjuvants which can be present in the compositions according to the invention are, for example, fatty substances, such as mineral, animal or vegetable oils or waxes; fatty acids; fatty acid esters, such as fatty acid triglycerides having from 6 to 18 carbon atoms; fatty alcohols; emulsifying agents, such as oxyethylenated fatty alcohols or polyglycerol alkyl ethers; solvents, such as lower monoalcohols or polyalcohols comprising from 1 to 6 carbon atoms; or water.

The mono- or polyalcohols which are more particularly preferred are chosen from ethanol, isopropanol, propylene glycol, glycerol and sorbitol.

Preferred fatty substances are mineral oils, of petrolatum; animal oils, of whale, shark, seal, menhaden, halibut liver, cod, tuna, tortoise, ox hoof, horse hoof, sheep hoof, mink, otter or marmot oils and vegetable oils, of almond, wheat germ, olive, maize germ, jojoba, sesame, sunflower, palm, walnut, karite, shorea, macadamia or blackcurrant seed oils.

Preferred fatty acid esters are, for example, esters of saturated or unsaturated $C_{12}$ to $C_{22}$ acids and of lower alcohols, such as isopropanol or glycerol, or of saturated or unsaturated, linear or branched $C_8$ to $C_{22}$ fatty alcohols or alternatively of $C_{10}$ to $C_{22}$ 1,2-alkanediols.

Preferred fatty substances are, for example, petrolatum, paraffin, lanolin, hydrogenated lanolin, tallow, acetylated lanolin or silicone oils.

Preferred waxes are, for example, Sipol wax, lanolin wax, beeswax, candelilla wax, microcrystalline wax, carnauba wax, spermaceti, cocoa butter, karite butter, silicone waxes, hydrogenated oils which are solid at 25° C., sucroglycerides, or calcium, magnesium and aluminium oleates, myristates, linoleates and stearates.

Preferred fatty alcohols are, for example, lauryl, cetyl, myristyl, stearyl, palmityl or oleyl alcohols and Guerbet alcohols, such as 2-octyldodecanol, 2-decyltetradecanol or 2-hexyldecanol.

Preferred emulsifying agents are, for example, polyoxyethylenated fatty alcohols, of lauryl, cetyl, stearyl and oleyl alcohols comprising from 2 to 20 mol of ethylene oxide and polyglycerol alkyl ethers, of $C_{12}$ to $C_{18}$ alcohols comprising from 2 to 10 mol of glycerol.

It may also be useful to use thickening agents, such as cellulose derivatives, polyacrylic acid derivatives, guar gum, locust bean gum or xanthan gum.

The compositions according to the invention may further comprise adjuvants commonly used in cosmetics or in dermatology and in particular moisturizing products, softeners, products for treating skin complaints, sunscreen agents, germicides, colorants, preservatives, fragrances and propellants.

When the compositions according to the invention are dispersions, they can be dispersions of compounds of formula (I) in water in the presence of surfactant or alternatively aqueous dispersions of lipid spherules composed of organized molecular layers enclosing an encapsulated aqueous phase, these layers being composed of at least one compound of formula (I) in combination with at least one other lipid compound.

Preferred lipid compounds are, for example, long-chain alcohols and diols, sterols, such as cholesterol, phospholipids, cholesteryl sulphate, cholesteryl phosphate, long-chain amines and their quaternary ammonium derivatives, dihydroxy- alkylamines, polyoxyethylenated fatty amines, long-chain aminoalcohol esters, salts thereof and quaternary ammonium derivatives, phosphoric esters of fatty alcohols, such as dicetyl hydrogen phosphate or its sodium salt, alkyl sulphates, such as sodium cetyl sulphate, fatty acids in the form of salts, or lipids of the type of those disclosed in French Patents Nos. 2,315,991, 1,477,048 and 2,091,516 or in International Patent Applications WO 83/01571 and WO 92/08685, the disclosures of which are specifically incorporated by reference herein.

Other lipids that may be used are lipids comprising a saturated or unsaturated, linear or branched, long lipophilic chain comprising 12 to 30 carbon atoms, for example an oleyl, lanolyl, tetradecyl, hexadecyl, isostearyl, lauryl or alkylphenyl chain. The hydrophilic group of these lipids can be an ionic or non-ionic group. Preferred non-ionic groups are, for example, groups derived from polyethylene glycol. Lipids that may be used to form the lamellar phase are, for example, polyglycerol ethers, such as those disclosed in French Patents Nos. 1,477,048, 2,091,516, 2,465,780 and 2,482,128, the disclosures of which are specifically incorporated by reference herein.

Ionic groups that may be used are, for example, groups derived from an amphoteric, anionic or cationic compound.

Other lipids disclosed in International Patent Application WO 83/01571, the disclosures of which are specifically incorporated by reference herein, that may be used for the formation of vesicles are glycolipids, such as lactosylceramide, galactocerebroside, gangliosides and trihexosylceramide, and phospholipids, such as phosphatidylglycerol and phosphatidylinositol.

One aspect of the invention is therefore a dispersion of lipid spherules composed of organized molecular layers of compounds of formula (I) and of lipids defined above including an aqueous phase to be encapsulated. The continuous phase of the dispersion which surrounds the spherules is an aqueous phase. The dispersed spherules generally have a diameter ranging from 0.05 microns to 5 microns. The aqueous phase encapsulated in the spherules can be water or an aqueous solution of active substance and, in this case, is preferably isoosmotic with respect to the continuous phase of the dispersion.

The spherules can be obtained in particular according to the process disclosed in French Patent 2,315,991, the disclosures of which are specifically incorporated by reference herein, according to which a dispersion of spherules composed of organized molecular layers including an aqueous phase to be encapsulated is prepared by combining mixtures of isomers of compounds of formula (I) in combination with one or more lipid(s) defined above with the aqueous phase to be encapsulated in these spherules, then stirring in order to ensure mixing and to obtain a lamellar phase, and subsequently adding a dispersion liquid in an amount greater than the amount of lamellar phase obtained, and finally vigorously shaking for a period of time ranging from 15 minutes to 3 hours approximately.

Another preparation process is called REV (reverse-phase evaporation vesicle), described in Proc. Natl. Acad. Sci. USA., Vol. 75, No. 9, pages 4194–4198 (1978), by Szoka and Papahadjopoulos, the disclosure of which is specifically incorporated by reference herein.

Another process that may be used comprises the sequence of dissolving at least one lipid in at least one water-immiscible organic solvent; adding the organic phase thus obtained to an aqueous phase; forming a dispersion of the two phases with vigorous stirring, it being possible for the size of the vesicles to be adjusted by varying the stirring speed during this phase mixing; evaporating the solvent(s) with vigorous stirring; and, if appropriate, concentrating the dispersion.

The active substances may be substances of pharmaceutical or food interest or substances having a cosmetic activity. When they are water-soluble, they are in the aqueous phase encapsulated inside the vesicles.

The water-soluble substances having a cosmetic and/or pharmaceutical activity may be products intended for caring for or treating the skin and hair, such as, for example, humectants, such as glycerol, sorbitol, pentaerythritol or pyrrolidonecarboxylic acid and its salts; artificial tanning agents, such as dihydroxyacetone, erythrulose, glyceraldehyde or γ-dialdehydes, such as tartaric aldehyde, these compounds are optionally used in combination with colorants; water-soluble sunscreen agents; antiperspirants, deodorants, astringents, freshening, tonic, cicatrizing, keratolytic or depilatory products, or scented waters; plant tissue extracts, such as polysaccahrides; water-soluble colorants; antidandruff agents; antiseborrhoeic agents; oxidizing agents, such as bleaching agents, for example aqueous hydrogen peroxide solution; or reducing agents, such as thioglycolic acid and its salts.

Additional water-soluble substances are, for example, vitamins, hormones, enzymes, such as superoxide dismutase, vaccines, antiinflammatory agents, such as hydrocortisone, antibiotics, bactericides or cytotoxic or antitumour agents.

When the active substances are liposoluble, they are found incorporated within the lamellae of the vesicles. They can be chosen from liposoluble sunscreen agents, substances intended to improve the state of dry or senile skin, tocopherols, vitamins E, F or A and their esters, retinoic acid, retinoids, antioxidants, essential fatty acids, glycyrrhetinic acid, keratolytic agents and carotenoids.

The dispersions of lipid spherules exhibit the advantage of conveying active substances, which are thus masked and protected with respect to various degrading agents: oxidizing agents and more generally compounds which are reactive with encapsulated active substances. The penetration and the fixing of the active substances can be modulated by varying the size of the spherules and their electric charge. The action of these active substances can also be deferred in this way (delay effect).

Another aspect of the invention is the use in cosmetics of an aqueous dispersion of spherules composed of organized molecular layers of compounds of formula (I), in combination with other lipids, including an aqueous phase to be encapsulated, in particular for the treatment of the skin.

Yet another aspect of the invention is the use of such a dispersion of lipid spherules in dermatology or in the food industry.

In what follows or what precedes, the percentages are given by weight, except when otherwise mentioned.

The examples which follow are given by way of illustration and without implied limitation. In these examples, A.M. means active material.

EXAMPLE 1

Preparation of N-(cholesteryloxycarbonyl)-2-aminooctadecane-1,3-diol 70 g (0.23 mol) of 2-aminooctadecane-1,3-diol are dissolved at 35° C. in 1 liter of tert-butyl methyl ether. After addition over 1 hour of 109 g (0.24 mol) of cholesteryl chloroformate and of 33.8 ml of triethanolamine, the reaction mixture is stirred for 4 hours at 35° C.

After extracting the organic phase, the latter is dried and evaporated to dryness. The crude product is crystallized from acetone to result in 114 g of the expected product (yield of 69%).

The $^{13}$C NMR spectrum and the elemental analysis of the product obtained are in accordance with the expected product with a melting point of 93–101° C.

Elemental analysis:

|        | C     | H     | N    | O    |
|--------|-------|-------|------|------|
| Theory | 77.36 | 11.71 | 1.96 | 8.96 |
| Found  | 77.24 | 11.64 | 1.82 | 9.21 |

EXAMPLE 2

Preparation of (4R,3S,2S)-N-(cholesteryloxycarbonyl)-2-aminooctadecane-1,3,4-triol 63 g (0.19 mol) of (4R,3S,2S)-2-aminooctadecane-1,3,4-triol are partially dissolved at 35° C. in 800 ml of tetrahydrofuran. After addition over 2 hours of 89.8 g (0.2 mol) of cholesteryl chloroformate and of 30 ml of triethylamine, the reaction mixture is stirred for 2 hours at 35° C.

After extracting the organic phase, the latter is dried and evaporated to dryness. The crude product is crystallized from ethyl acetate to result in 122 g of the expected product (yield of 83%).

The $^{13}$C NMR spectrum and the elemental analysis of the product obtained are in accordance with the expected product with a melting point of 135–148° C.

Elemental analysis:

|        | C     | H     | N    | O     |
|--------|-------|-------|------|-------|
| Theory | 75.67 | 11.46 | 1.92 | 10.96 |
| Found  | 75.23 | 11.33 | 1.82 | 11.69 |

EXAMPLE 3

Shampoo

Alkylpolyglucoside, sold under the name KAG 40 by the company KAO, comprising

| | |
|---|---|
| 40% of active material | 10 g AM |
| Sodium lauryl amido ether carboxylate (3 EO), sold under the name Akypo Focum 30 BV by the company CHEM'Y | 5 g AM |
| Diurethane of oxyethylenated (6 EO) and oxypropylenated (14 PO) alcohols ($C_{16}/C_{18}$), sold under the name Elfacos T212 by the company AKZO | 2.5 g AM |
| Compound of Example 1 | 0.1 g |
| Preservative, fragrance, HCl pH 6 | q.s. |
| Water | q.s. for 100 g |

EXAMPLE 4

Rinse-out Caring Conditioner

| | |
|---|---|
| 1-Methyl-2-tallow-3-tallowamidoethyl-imidazolium methyl sulphate/propylene glycol (75/25), sold by Witco under the name of Rewoquat W75PG | 2.6 g AM |
| Compound of Example 1 | 0.5 g |
| Mixture of oxyethylenated cetyl/stearyl and cetyl alcohol | 2.5 g |
| Preservative, fragrance | q.s. |
| Water | q.s. for 100 g |

Spontaneous pH of 3.8

EXAMPLE 5

Measurement of the Imperceptible Water Loss (IWL)

This measurement is made using an evaporimeter (Servomed) which quantitatively determines the evaporation of water, that is to say diffusional water transportation, from a sample of stratum corneum, delipidated beforehand, sealing a cylindrical capsule comprising water; the entire assembly being placed in a chamber at controlled relative temperature a and controlled relative humidity.

Sensors make it possible to measure the partial vapor pressure of water at two points situated at different distances from the sample. The partial vapor pressure of water gradient between the two points is thus determined and thus the rate of evaporation in accordance with Fick's law.

A comparative test was carried out on the effects on the IWL of a 1% by weight solution in isopropanol of compound A, corresponding to that of Example 1, with respect to a solution comprising, instead of the compound according to the invention, the compound B, which is the N-(hexadecyloxycarbonyl)-2-aminooctadecane-1,3-diol disclosed in French Patent 2,652,002, the disclosures of which are specifically incorporated by reference herein.

The results are combined in the following table.

| Compound | Composition (concentration) | IWL, 20 H (%) |
|---|---|---|
| A (invention) | 1% in isopropanol | −6 +/− 2 |
| B (not according to the invention) | 1% in isopropanol | 0 +/− 2 |

It is thus found that the application of the compounds according to the invention makes it possible to significantly reduce the loss of water present in the stratum corneum, thus demonstrating improved barrier properties, for the compounds according to the invention, to permeability to stratum corneum water.

What is claimed is:

1. A compound of formula (I):

$$R_1-CHOH-CH(NH-COOR_2)-CH_2OH \quad (I)$$

in which:

R$_1$ denotes a C$_1$ to C$_{31}$ hydrocarbon-comprising radical, and OR$_2$ denotes a cholesteryl radical, said compound being in the pure form or in the form of a mixture of isomers.

2. The compound according to claim 1, wherein R$_1$ denotes a saturated or unsaturated, linear or branched C$_9$ to C$_{25}$ hydrocarbon radical.

3. The compound according to claim 2, wherein R$_1$ denotes a saturated or unsaturated, linear or branched C$_9$ to C$_{25}$ hydrocarbon radical which can be substituted by one or more optionally esterified hydroxyls.

4. The compound according to claim 1, wherein said compound is chosen from:

N-(cholesteryloxycarbonyl)-2-aminooctadecane-1,3-diol and

N-(cholesteryloxycarbonyl)-2-aminooctadecane-1,3,4-triol, said compound being in the pure form or in the form of mixtures of isomers.

5. A composition comprising at least one compound according to claim 1, wherein said composition is in the form of a milk or cream emulsion; an aqueous/alcoholic, oily, or oleoalcoholic lotion; a gel; a dispersion; a solid stick; lipid spherules or an aerosol foam or spray.

6. The composition according to claim 5, wherein said emulsion is a water-in-oil or oil-in-water emulsion, each comprising a fatty and aqueous phase.

7. The composition according to claim 6, wherein said fatty phase of the emulsion represents from 5 to 60% of the total weight of the emulsion.

8. The composition according to claim 6, wherein said aqueous phase of the emulsion represents from 30 to 85% of the total weight of the emulsion.

9. The composition according to claim 6, wherein said emulsion comprises at least one emulsifying agent in an amount ranging from 1 to 20% of the total weight of the emulsion.

10. The composition according to claim 9, wherein said at least one emulsifying agent is present in an amount ranging from 2 to 12%.

11. A process for the preparation of the compound of formula (I) according to claim 1 comprising the step of reacting the amine functional group of a sphingoid base of formula (II):

$$R_1-CHOH-CH(NH_2)-CH_2OH \quad (II)$$

in which R$_1$ has the same meaning indicated in formula (I) with either a cholesteryl chloroformate of formula (III):

$$R_2-O-C(=O)-Cl \quad (III)$$

in which OR$_2$ has the same meaning indicated in formula (I), in an appropriate organic solvent in the presence of a base; or with a cholesteryl imidazolide of formula (IV):

$$R_2-O-C(=O)-N(\text{imidazolyl}) \quad (IV)$$

in which OR$_2$ has the same meaning indicated in the formula (I).

12. The process according to claim 11, wherein said organic solvent is chosen from tert-butyl methyl ether, dimethylformamide and tetrahydrofuran.

13. The process according to claim 11, wherein said base is chosen from triethylamine, pyridine and sodium bicarbonate.

14. A process for the cosmetic treatment of the skin, hair, nails, eyelashes or eyebrows which comprising applying to said skin, hair, nails, eyelashes or eyebrows an effective amount of a compound according to claim 1.

15. A composition comprising at least one compound of formula (I) according to claim 1 and a cosmetically acceptable medium.

16. A composition according to claim 15, wherein said at least one compound of formula (I) is present in an amount ranging from 0.005 to 20% by weight, with respect to the total weight of the composition.

17. A composition according to claim 16, wherein said compound of formula (I) is present in an amount ranging from 0.01 to 10%.

18. A composition according to claim 15, said composition being in the form of an emulsion; an aqueous/alcoholic, oleoalcoholic or oily lotion; a gel; a dispersion; solid sticks; or an aerosol foam or spray.

19. A composition according to claim 15, wherein said composition further comprises at least one adjuvant chosen from fatty substances, emulsifying agents, solvents, water, moisturizing products, softeners, products for treating skin complaints, sunscreen agents, germicides, colorants, preservatives, fragrances and propellants.

20. A composition according to claim 19, wherein said fatty substances are chosen from mineral, animal and vegetable oils, waxes, fatty acids, fatty acid esters and fatty alcohols.

21. The composition according to claim 20, wherein said mineral, animal and vegetable oils are chosen from mineral oils of petrolatum; animal oils of whale, shark, seal, menhaden, halibut liver, cod, tuna, tortoise, ox hoof, horse hoof, sheep hoof, mink, otter and marmot; vegetable oils of almond, wheat germ, olive, maize germ, jojoba, sesame, sunflower, palm, walnut, karite, shorea, macadamia and blackcurrant seed; and petrolatum, paraffin, lanolin, hydrogenated lanolin, tallow, acetylated lanolin and silicone oils.

22. The composition according to claim 20, wherein said waxes are chosen from Sipol wax, lanolin wax, beeswax, candelilla wax, microcrystalline wax, carnauba wax, spermaceti, cocoa butter, karite butter, silicone waxes, hydrogenated oils which are solid at 25° C., sucroglycerides, and calcium, magnesium and aluminium oleates, myristates, linoleates and stearates.

23. The composition according to claim 20, wherein said fatty acid esters are chosen from esters of saturated and unsaturated $C_{12}$ to $C_{22}$ acids and lower alcohols, and esters of saturated and unsaturated, linear and branched $C_8$ to $C_{22}$ fatty alcohols and $C_{10}$ to $C_{22}$ 1,2-alkanediols.

24. The composition according to claim 20, wherein said fatty alcohols are chosen from lauryl, cetyl, myristyl, stearyl, palmityl and oleyl alcohols.

25. The composition according to claim 24, wherein said fatty alcohols are chosen from 2-octyldodecanol, 2-decyltetradecanol and 2-hexyldecanol.

26. The composition according to claim 19, wherein said emulsifying agents are chosen from polyoxyethylenated fatty alcohols and polyglycerol alkyl ethers.

27. The composition according to claim 15, wherein said composition further comprises thickening agents chosen from cellulose derivatives, polyacrylic acid derivatives, guar gum, locust bean gum and xanthan gum.

28. A composition for cosmetic use, wherein said composition is in the form of an aqueous dispersion of lipid spherules composed of organized molecular layers enclosing an encapsulated aqueous phase, said layers comprising at least one compound of formula (I) according to claim 1 in combination with at least one other lipid compound.

29. A composition in the form of an aqueous dispersion of lipid spherules according to claim 28, wherein said at least one other lipid compound is chosen from long-chain alcohols and diols, sterols, phospholipids, glycolipids, cholesteryl sulphate, cholesteryl phosphate, long-chain amines and their quaternary ammonium derivatives, dihydroxyalkylamines, polyoxyethylenated fatty amines, long-chain aminoalcohol esters and their salts and quaternary ammonium derivatives thereof, phosphoric esters of fatty alcohols, alkyl sulphates, fatty acids in the form of salts, and saturated and unsaturated, linear and branched, long lipophilic chain comprising 12 to 30 carbon atoms.

30. A composition according to claim 28, wherein said encapsulated aqueous phase additionally comprises at least one water-soluble or liposoluble active substance.

31. The composition according to claim 30, wherein said water-soluble active substance is chosen from humectants, artificial tanning agents, water-soluble sunscreen agents, antiperspirants, deodorants, astringents, freshening, tonic, cicatrizing, keratolytic and depilatory products, scented waters, plant tissue extracts, water-soluble colorants, antidandruff agents, antiseborrhoeic agents, oxidizing agents, reducing agents, vitamins, hormones, enzymes, vaccines, antiinflammatory agents, antibiotics, bactericides, and cytotoxic and antitumour agents.

32. The composition according to claim 30, wherein said at least one liposoluble active substance is chosen from liposoluble sunscreen agents, substances intended to improve the state of dry or senile skin, tocopherols, vitamins E, F and A and their esters, retinoic acid, retinoids, antioxidants, essential fatty acids, glycyrrhetinic acid, keratolytic agents and carotenoids.

33. A composition in the form of an aqueous dispersion of lipid spherules according to claim 28, wherein said spherules have a diameter from 0.05 to 5 microns.

34. A cosmetic composition comprising a compound of formula (I) according to claim 1 as a moisturizing agent.

35. A method of forming a dispersion of lipid spherules for cosmetic use comprising combining a compound of formula (I) according to claim 1 with at least one other lipid compound.

36. A process for the cosmetic moisturizing treatment of the skin, hair, nails or eyelashes comprising applying to said skin, hair, nails or eyelashes an effective amount of a composition according to claim 1.

* * * * *